United States Patent
Sakurai et al.

(10) Patent No.: US 10,263,042 B2
(45) Date of Patent: Apr. 16, 2019

(54) ORGANIC PHOTOELECTRIC DEVICE AND IMAGE SENSOR

(71) Applicant: Samsung Electronics Co., Ltd., Suwon-si, Gyeonggi-do (KR)

(72) Inventors: Rie Sakurai, Suwon-si (KR); Hiromasa Shibuya, Seongnam-si (KR); Tadao Yagi, Hwaseong-si (KR); Kwang Hee Lee, Yongin-si (KR); Takkyun Ro, Hwaseong-si (KR); Sung Young Yun, Suwon-si (KR); Gae Hwang Lee, Seongnam-si (KR); Dong-Seok Leem, Hwaseong-si (KR); Seon-Jeong Lim, Yongin-si (KR); Xavier Bulliard, Seongnam-si (KR); Yong Wan Jin, Seoul (KR); Yeong Suk Choi, Suwon-si (KR); Hye Sung Choi, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 3 days.

(21) Appl. No.: 15/255,649

(22) Filed: Sep. 2, 2016

(65) Prior Publication Data

US 2017/0069690 A1 Mar. 9, 2017

(30) Foreign Application Priority Data

Sep. 4, 2015 (KR) .................. 10-2015-0125838

(51) Int. Cl.
*H01L 27/30* (2006.01)
*H01L 51/00* (2006.01)
(Continued)

(52) U.S. Cl.
CPC .......... *H01L 27/307* (2013.01); *C07D 403/04* (2013.01); *C07D 403/14* (2013.01);
(Continued)

(58) Field of Classification Search
CPC .. C07D 403/04; C07D 403/14; C07D 471/04; C07D 487/04; H01L 27/307;
(Continued)

(56) References Cited

U.S. PATENT DOCUMENTS 6,087,258 A 7/2000 Simpson et al.
6,824,952 B1 11/2004 Minsek et al.
(Continued)

FOREIGN PATENT DOCUMENTS

CN 104230953 A 12/2014
JP H09-311232 A 12/1997
(Continued)

OTHER PUBLICATIONS

Marzena Grucela-Zajac et al., "(Photo)physical Properties of New Molecular Glasses End-Capped with Thiophene Rings Composed of Diimide and Imine Units", The Journal of Physical Chemistry, May 21, 2014, pp. 13070-13086, ACS Author Choice.*
(Continued)

*Primary Examiner* — Tom Thomas
*Assistant Examiner* — Benjamin T Liu
(74) *Attorney, Agent, or Firm* — Harness, Dickey & Pierce, P.L.C.

(57) ABSTRACT

An organic photoelectric device includes a first electrode and a second electrode facing each other, and an active layer between the first electrode and the second electrode, wherein the active layer includes an n-type semiconductor compound that is transparent in a visible ray region and represented by Chemical Formula 1, and a p-type semiconductor compound having a maximum absorption wavelength in a wavelength region of about 500 nm to about 600 nm of a visible ray region.

16 Claims, 6 Drawing Sheets

(51) Int. Cl.
*C07D 403/04* (2006.01)
*C07D 403/14* (2006.01)
*C07D 471/04* (2006.01)
*C07D 487/04* (2006.01)
*H01L 51/42* (2006.01)

(52) U.S. Cl.
CPC ........ *C07D 471/04* (2013.01); *C07D 487/04* (2013.01); *H01L 51/0032* (2013.01); *H01L 51/0053* (2013.01); *H01L 51/0067* (2013.01); *H01L 51/006* (2013.01); *H01L 51/0061* (2013.01); *H01L 51/4253* (2013.01)

(58) Field of Classification Search
CPC ............. H01L 51/0032; H01L 51/0053; H01L 51/0067; H01L 51/4253; H01L 51/0061; H01L 51/006
See application file for complete search history.

(56) References Cited

U.S. PATENT DOCUMENTS

| | | |
|---|---|---|
| 7,141,863 B1 | 11/2006 | Compaan et al. |
| 7,973,307 B2 | 7/2011 | Rand et al. |
| 2016/0064672 A1* | 3/2016 | Lee .................... H01L 51/0021 257/40 |
| 2016/0268401 A1* | 9/2016 | Aleksov .............. H01L 51/0533 |
| 2017/0074652 A1* | 3/2017 | Send ........................ G01C 3/08 |

FOREIGN PATENT DOCUMENTS

| | | |
|---|---|---|
| JP | H10-91384 A | 4/1998 |
| JP | 2009-274966 A | 11/2009 |
| JP | 2012-123292 A | 6/2012 |
| JP | 2012-151761 A | 8/2012 |
| JP | 2013-040147 A | 2/2013 |
| JP | 2014-210768 A | 11/2014 |
| WO | WO-2008-091670 A2 | 7/2008 |
| WO | WO-2010-011658 A2 | 1/2010 |

OTHER PUBLICATIONS

Satoshi Aihara et al., "Stacked Image SensorWith Green- and Red-Sensitive Organic Photoconductive Films Applying Zinc Oxide Thin-Film Transistors to a Signal Readout Circuit", IEEE Transactions on Electron Devices, vol. 56, No. 11, Nov. 2009, pp. 2570-2576.*
Gorkem Memisoglu et al., "Highly Efficient Organic UV Photodetectors Based on Polyfluorene and Naphthalenediimide Blends: Effect of Thermal Annealing", 2012, International Journal of Photoenergy vol. 2012, Article ID 936075, 11 pages, Hindawi Publishing Corporation.
Jiri Misek et al., "A Chiral and Colorful Redox Switch: Enhanced p Acidity in Action", 2010, Angew. Chem. Int. Ed. 2010, 49, 7680-7683, Wiley-VCH Verlag GmbH & Co. KGaA, Weinheim.
Hokuto Seo et al., "Color Sensors with Three Vertically Stacked Organic Photodetectors", Japanese Journal of Applied Physics vol. 46, No. 49, 2007, pp. L1240-L1242, The Japan Society of Applied Physics.
Mikio Ihama et al., "CMOS Image Sensor with a Thin Overlaid Panchromatic Organic Photoconductive Layer for Sensors with Reduced Pixel Size", IDW'09, INP1-4, pp. 2123-2126.

* cited by examiner

ORGANIC PHOTOELECTRIC DEVICE AND IMAGE SENSOR

RELATED APPLICATIONS

This application claims the benefit of priority from Korean Patent Application No. 10-2015-0125838, filed in the Korean Intellectual Property Office on Sep. 4, 2015, the entire contents of which are incorporated herein by reference.

BACKGROUND

1. Field

Example embodiments relate to an organic photoelectric device and an image sensor.

2. Description of the Related Art

A photoelectric device typically converts light into an electrical signal using photoelectric effects. The photoelectric device may include a photodiode, a phototransistor, and the like, and may be part of an image sensor, a solar cell, an organic light emitting diode, and the like.

An image sensor including a photodiode typically requires high resolution and thus a small pixel. At present, silicon photodiodes are widely used, but present a problem of deteriorated sensitivity because of a small absorption area due to small pixels. Accordingly, an organic material that is capable of replacing silicon has been researched.

The organic material typically has a high extinction coefficient and selectively absorbs light in a particular wavelength region depending on a molecular structure, and thus may replace both a photodiode and a color filter, and improve sensitivity and contribute to high integration as a result.

SUMMARY

An example embodiment includes an organic photoelectric device having high photoelectric conversion efficiency and wavelength selectivity.

Another example embodiment includes an image sensor including the organic photoelectric device.

According to an example embodiment, an organic photoelectric device includes a first electrode and a second electrode facing each other and an active layer interposed between the first electrode and the second electrode, wherein the active layer includes an n-type semiconductor compound that is transparent in a visible ray region and represented by Chemical Formula 1, and a p-type semiconductor compound having a maximum absorption wavelength in a wavelength region of about 500 nm to about 600 nm of a visible ray region.

[Chemical Formula 1]

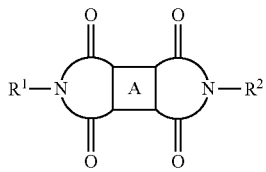

In Chemical Formula 1,

A is one of a substituted or unsubstituted C6 to C30 aromatic ring group, a substituted or unsubstituted C4 to C30 alicyclic group, a substituted or unsubstituted C3 to C30 hetero aromatic ring group, a substituted or unsubstituted C4 to C30 heteroalicyclic group, and a combination thereof, and $R^1$ and $R^2$ are independently one of a substituted or unsubstituted C6 to C30 aryl group, a substituted or unsubstituted C3 to C30 heteroaryl group, and a combination thereof.

In Chemical Formula 1, $R^1$ and $R^2$ may be represented by Chemical Formula A.

[Chemical Formula A]

(1)

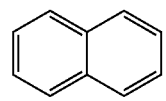

(2)

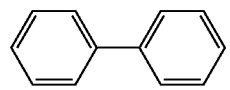

(3)

(4)

(5)

(6)

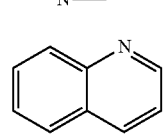

(7)

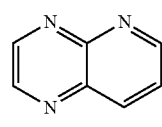

(8)

(9)

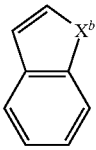

(10)

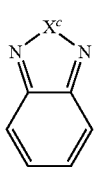

(11)

(12)

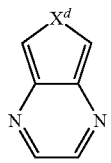

In Chemical Formula A, $X^a$, $X^b$, $X^c$, and $X^d$ are independently one of O, S, Se, Te, S(=O), S(=O)$_2$, and SiR$^a$R$^b$ (wherein R$^a$ and R$^b$ is hydrogen or a C1 to C10 alkyl group), and the hydrogen (H) of each ring of Chemical Formula A may be replaced by a substituent selected from a C1 to C10 linear or branched alkyl group, a halogen, and a cyano group.

The n-type semiconductor compound may have an energy bandgap that is greater than or equal to about 2.8 eV.

The n-type semiconductor compound may not substantially absorb visible light in a wavelength region of greater than or equal to about 400 nm to less than or equal to about 700 nm.

The n-type semiconductor compound may have a Highest Occupied Molecular Orbital (HOMO) level that is greater than about 6.0 eV.

A difference between a HOMO level of the n-type semiconductor compound and a work function of the second electrode may be greater than or equal to about 1.5 eV.

The n-type semiconductor compound may be represented by one of Chemical Formulae 1a to 1e.

[Chemical Formula 1a]

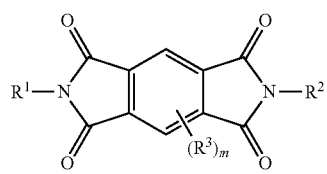

[Chemical Formula 1b]

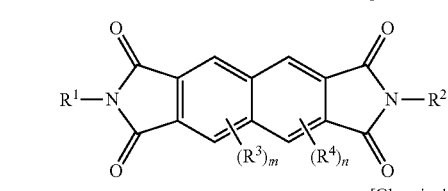

[Chemical Formula 1c]

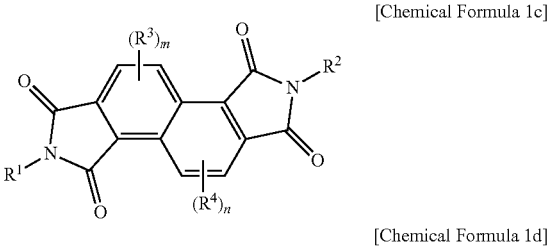

[Chemical Formula 1d]

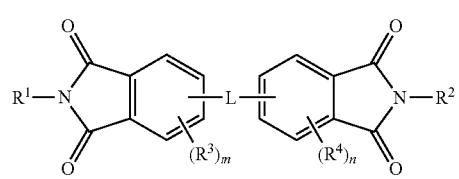

[Chemical Formula 1e]

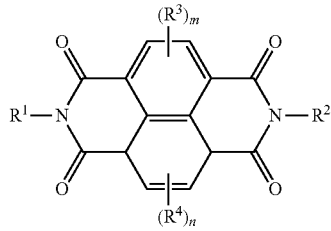

In Chemical Formulae 1a to 1e,

R$^1$ and R$^2$ are the same as R$^1$ and R$^2$ of Chemical Formula 1, R$^3$ and R$^4$ are independently one of a halogen (F, Br, Cl or I), a C1 to C10 haloalkyl group, a nitro group, a cyano group, a C1 to C10 alkoxy group, and a C1 to C10 alkyl group, L is one of a C1 to C4 alkylene, a fluoro-substituted C1 to C4 alkylene, phenylene, S, S(=O), S(=O)$_2$, O, and C(=O), and m and n are independently an integer ranging from 0 to 2.

The p-type semiconductor compound may be selected from N,N'-dimethylquinacridone (DMQA), N,N'-dimethyl-2,9-dimethylquinacridone (DMMQA), a compound represented by Chemical Formula 2, a compound represented by Chemical Formula 3, and a combination thereof.

[Chemical Formula 2]

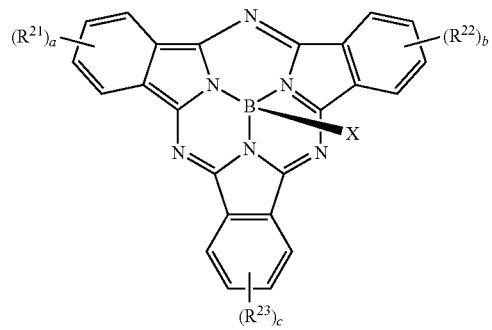

In Chemical Formula 2,

R$^{21}$ to R$^{23}$ are independently one of hydrogen, a substituted or unsubstituted C1 to C30 alkyl group, a substituted or unsubstituted C6 to C30 aryl group, a substituted or unsubstituted C3 to C30 heteroaryl group, a halide group, a halogen-containing group, and a combination thereof, a, b, and c are independently an integer ranging from 1 to 3, and X is an anion.

[Chemical Formula 3]

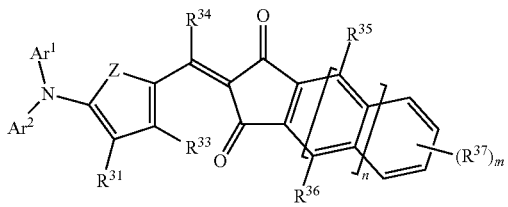

In Chemical Formula 3,

Z is one of S, Se, Te, S(=O), S(=O)$_2$ and SiR$^a$R$^b$ (wherein R$^a$ and R$^b$ is hydrogen or a C1 to C10 alkyl group), Ar$^1$ and Ar$^2$ are each one of a substituted or unsubstituted C6 to C30 aryl group and a substituted or unsubstituted C4 to C30 heteroaryl group, $R^{31}$ to $R^{37}$ are independently one of hydrogen, a substituted or unsubstituted C1 to C30 alkyl group, a substituted or unsubstituted C6 to C30 aryl group, a substituted or unsubstituted C4 to C30 heteroaryl group, a halide group, and a cyano group (CN), m is an integer ranging from 0 to 4, and n is 0 or 1.

The p-type semiconductor compound may have an energy bandgap that is greater than or equal to about 2.0 eV and less than or equal to about 2.5 eV.

The p-type semiconductor compound may have a maximum absorption wavelength ($\lambda_{max}$) that is greater than or equal to about 530 nm and less than or equal to about 600 nm.

The active layer may selectively absorb light in a green wavelength region.

A hole blocking layer may not be present between the first electrode and the active layer, or between the second electrode and the active layer.

Another example embodiment includes an image sensor including the organic photoelectric device discussed above.

The image sensor may include a semiconductor substrate integrated with a first photo-sensing device configured to sense light in a blue wavelength region, and a second photo-sensing device configured to sense light in a red wavelength region, and the organic photoelectric device on the semiconductor substrate configured to absorb light in a green wavelength region.

The first photo-sensing device and the second photo-sensing device may be positioned at a different depth from the surface of the semiconductor substrate.

The image sensor may further include a color filter layer on or under the organic photoelectric device.

The color filter layer may be positioned between the semiconductor substrate and the organic photoelectric device, and may include a first color filter positioned corresponding to the first photo-sensing device and configured to selectively transmit light in a blue region, and a second color filter positioned corresponding to the second photo-sensing device and configured to selectively transmit light in a red region.

DETAILED DESCRIPTION

Figure 1:
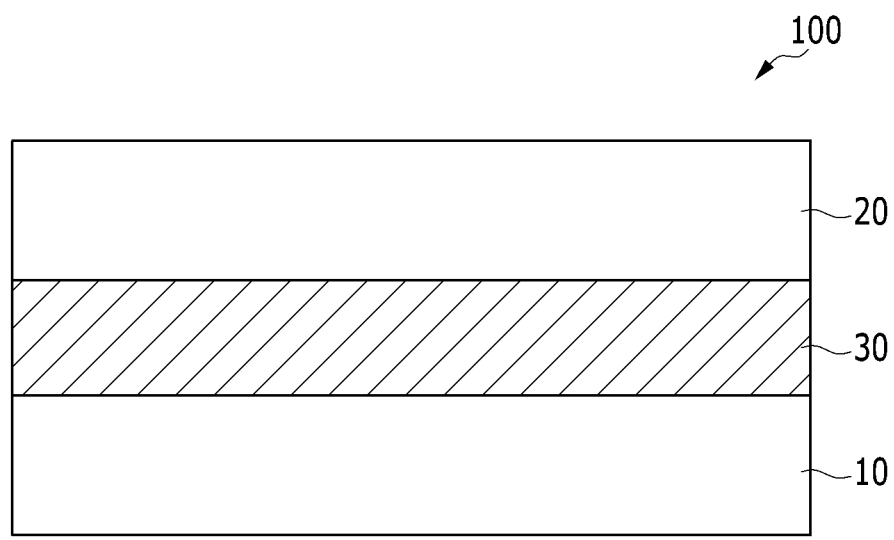
FIG. 1 is a cross-sectional view illustrating an organic photoelectric device according to an example embodiment.

Example embodiments will hereinafter be described in detail, and may be easily performed by those who have common knowledge in the related art. However, this disclosure may be embodied in many different forms and is not construed as limited to the example embodiments set forth herein.

As used herein, when a definition is not otherwise provided, the term "substituted" refers to one substituted with at least a functional group selected from a halogen (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof, instead of hydrogen of a compound.

As used herein, when specific definition is not otherwise provided, the term "hetero" refers to one including 1 to 3 heteroatoms selected from N, O, S, and P.

As used herein, when a definition is not otherwise provided, the term "halide group" or "halogen" refers to —F, —Cl, —Br or —I, and the term "halogen-containing group" is a group where at least one hydrogen is replaced by —F, —Cl, —Br, or —I. For example, a haloalkyl group refers to an alkyl group where at least one hydrogen is replaced by F, Cl, Br, or I. Specific examples of a haloalkyl group may be a fluoroalkyl group, for example a perfluoroalkyl group.

In the drawings, the thickness of layers, films, panels, regions, etc., are exaggerated for clarity. Like reference numerals designate like elements throughout the specification. It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

In the drawings, parts having no relationship with the description are omitted for clarity of the example embodiments, and the same or similar constituent elements are indicated by the same reference numerals throughout the specification.

Hereinafter, referring to the drawings, an organic photoelectric device according to an example embodiment is described.

FIG. 1 is a cross-sectional view showing an organic photoelectric device according to an example embodiment.

Referring to FIG. 1, an organic photoelectric device 100 according to an example embodiment includes a first electrode 10 and a second electrode 20 facing each other, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be or include, for example, a transparent conductor such as indium tin oxide (ITO) or indium zinc oxide (IZO), or a metal thin layer of a thin monolayer or multilayer. When one of the first electrode 10 and the second electrode 20 is a non-light-transmitting electrode, it may be made of or include, for example, an opaque conductor such as aluminum (Al).

The active layer 30 may include a mixed n-type semiconductor material and p-type semiconductor material to form a pn junction, and receives external light, produces excitons, and separates the excitons into holes and electrons.

The active layer 30 may include an n-type semiconductor compound being transparent in a visible ray region and represented by Chemical Formula 1, and a p-type semiconductor compound having a maximum absorption wavelength in a wavelength region of about 500 nm to about 600 nm of a visible ray region.

[Chemical Formula 1]

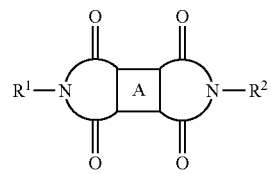

In Chemical Formula 1,

A is one of a substituted or unsubstituted C6 to C30 aromatic ring group, a substituted or unsubstituted C4 to C30 alicyclic group, a substituted or unsubstituted C3 to C30 hetero aromatic ring group, a substituted or unsubstituted C4 to C30 heteroalicyclic group, and a combination thereof, $R^1$ and $R^2$ are independently one of a substituted or unsubstituted C6 to C30 aryl group, a substituted or unsubstituted C3 to C30 heteroaryl group, and a combination thereof.

The aromatic ring group or the hetero aromatic ring group represented by A in Chemical Formula 1 may be a substituted or unsubstituted monocyclic aromatic group or hetero aromatic group substituted or unsubstituted condensed polycyclic aromatic group or hetero aromatic group, or a substituted or unsubstituted non-condensed polycyclic aromatic group or hetero aromatic group. Herein, the substituted monocyclic aromatic group or hetero aromatic group, the condensed polycyclic aromatic group or hetero aromatic group, or the non-condensed polycyclic aromatic group or hetero aromatic group may have a substituent selected from halogen (F, Br, Cl or I), a C1 to C10 haloalkyl group, a nitro group, a cyano group, a C1 to C10 alkoxy group, and a C1 to C10 alkyl group. The monocyclic aromatic group refers to a carbocyclic aromatic system including one ring. The condensed polycyclic aromatic group refers to an aromatic system where rings condensed one another. The non-condensed polycyclic aromatic group refers to an aromatic system where several rings are linked directly or through a linker. Herein, the linker may be C1 to C4 alkylene, C1 to C4 alkylene substituted with fluoro, phenylene, S, S(=O), S(=O)2, O, or C(=O).

The hetero aromatic ring group refers to an aromatic ring group including greater than or equal to about one hetero atom selected from N, O, and S inside the ring. Herein, the aromatic ring group is the same as described above.

In an example embodiment, the A may be a substituted or unsubstituted C6 to C30 arylene group or a substituted or unsubstituted C3 to C30 heteroarylene group, for example substituted or unsubstituted C6 to C14 arylene group or a substituted or unsubstituted C3 to C12 heteroarylene group.

In an example embodiment, the A may be a substituted or unsubstituted C4 to C30 cycloalkyl group, a substituted or unsubstituted C4 to C30 cycloalkenyl group, a substituted or unsubstituted C4 to C30 heterocycloalkyl group, or a substituted or unsubstituted C4 to C30 heterocycloalkenyl group, for example substituted or unsubstituted C4 to C14 cycloalkyl group, a substituted or unsubstituted C4 to C14 cycloalkenyl group, a substituted or unsubstituted C4 to C14 heterocycloalkyl group, or a substituted or unsubstituted C4 to C14 heterocycloalkenyl group.

In Chemical Formula 1, R1 and R2 are a substituted or unsubstituted C6 to C30 aryl group or a substituted or unsubstituted C3 to C30 heteroaryl group that is directly linked to an N-containing imide ring. In this way, when the R1 and R2 are directly linked to the N-containing imide ring, thermal stability may be improved.

In Chemical Formula 1, examples of R1 and R2 may be a functional group represented by Chemical Formula A.

[Chemical Formula A]

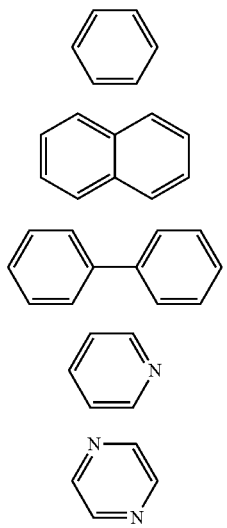

(1)

(2)

(3)

(4)

(5)

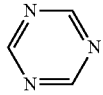

(6)

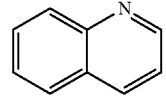

(7)

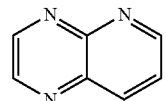

(8)

(9)

(10)

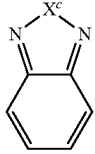

(11)

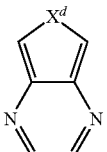

(12)

In Chemical Formula A, $X^a$, $X^b$, $X^c$, and $X^d$ are each independently selected from O, S, Se, Te, S(=O), S(=O)$_2$, and SiR$^a$R$^b$ (wherein R$^a$ and R$^b$ is hydrogen or a C1 to C10 alkyl group), and hydrogen of each ring of Chemical Formula A is optionally replaced by a substituent selected from a C1 to C10 linear or branched alkyl group, a halogen and a cyano group.

The functional group represented by Chemical Formula A has no particular limit about a position bound at N of Chemical Formula 1.

In at least one example embodiment, the n-type semiconductor compound has transparency, is configured to transmit light in a visible light region and is not configured to substantially absorb visible light in a wavelength region ranging from greater than or equal to about 350 nm to less than or equal to about 750 nm, for example, greater than or equal to less than or equal to about 400 nm to less than or equal to about 700 nm, greater than or equal to less than or equal to about 450 nm to about 700 nm, or greater than or equal to about 400 nm and less than about 500 nm. Herein, no substantial absorption indicates that an absorption coefficient is in a range of less than or equal to about 40000 cm$^{-1}$ within the wavelength ranges. The n-type semiconductor compound absorbs light in an ultraviolet (UV) region but not light in a visible light region. In an example embodiment, the n-type semiconductor compound has an absorption coefficient of less than or equal to about 40000 cm$^{-1}$, for example, less than or equal to about 20000 cm$^{-1}$ at greater than or equal to about 400 nm and less than 500 nm, for example, about 420 to about 480 nm, for example, about 450 nm. Accordingly, absorption selectivity in a green wavelength region may be improved by largely reducing absorption in a blue light region.

The n-type semiconductor compound may have an energy bandgap that is greater than or equal to about 2.8 eV, for example, greater than or equal to about 3.0 eV and less than or equal to about 4.0 eV and a HOMO level ranging from greater than about 6.0 eV to less than about 8.5 eV.

In addition, the HOMO level of the n-type semiconductor compound and the work function of the second electrode 20 may have a difference that is greater than or equal to about 1.5 eV, for example, greater than or equal to about 1.8 eV. Herein, the HOMO level indicates an absolute value of the HOMO level when a vacuum level is 0 eV. Accordingly, the n-type semiconductor compound may block holes flowing in from the outside. Accordingly, a hole blocking layer may not be disposed between a cathode and the active layer 30.

The n-type semiconductor compound may be represented by one of Chemical Formulae 1a to 1e, but is not limited thereto.

[Chemical Formula 1a]

[Chemical Formula 1b]

[Chemical Formula 1c]

[Chemical Formula 1d]

[Chemical Formula 1e]

In Chemical Formulae 1a to 1e,
$R^1$ and $R^2$ are the same as $R^1$ and $R^2$ in Chemical Formula 1, $R^3$ and $R^4$ are each independently selected from a halogen (F, Br, Cl or I), C1 to C10 haloalkyl group, a nitro group, a cyano group, C1 to C10 alkoxy group, and a C1 to C10 alkyl group, L is one of a C1 to C4 alkylene, a fluoro-substituted C1 to C4 alkylene, phenylene, S, S(=O), S(=O)$_2$, O, and C(=O), and m and n are independently an integer ranging from 0 to 2.

The n-type semiconductor compound of Chemical Formula 1 may be prepared by reacting dianhydride and amine.

The p-type semiconductor compound is a visible light absorber having a maximum absorption wavelength (λmax) in a range of about 500 nm to about 600 nm, for example in a range of greater than or equal to about 520 nm to less than or equal to about 600 nm, or in a range of greater than or equal to about 530 nm to less than or equal to about 600 nm.

The p-type semiconductor compound may for example have an energy bandgap that is greater than or equal to about 2.0 eV and less than or equal to about 2.5 eV.

For example, the p-type semiconductor compound may be one of N,N'-dimethylquinacridone (DMQA), N,N'-dimethyl-2,9-dimethylquinacridone (DMMQA), a compound represented by Chemical Formula 2, a compound represented by Chemical Formula 3, and a combination thereof.

[Chemical Formula 2]

In Chemical Formula 2, $R^{21}$ to $R^{23}$ are independently one of hydrogen, a substituted or unsubstituted C1 to C30 alkyl group, a substituted or unsubstituted C6 to C30 aryl group, a substituted or unsubstituted C3 to C30 heteroaryl group, a halide group, a halogen-containing group, or a combination thereof, a, b, and c are independently an integer ranging from 1 to 3, and X is an anion.

The X may be a halide group, for example —F or —Cl, or —Si(Ra)(Rb) (Rc).

The Ra, Rb, and Rc may each independently be a substituted or unsubstituted C1 to C30 alkyl group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group, a substituted or unsubstituted C6 to C30 arylamine group, a substituted or unsubstituted silyl group, or a combination thereof.

In Chemical Formula 2, R21 to R23 may be an electron donating functional group selected from a substituted or unsubstituted C1 to C30 alkyl group, a substituted or unsubstituted C6 to C30 aryl group, and a substituted or unsubstituted C3 to C30 heteroaryl group.

[Chemical Formula 3]

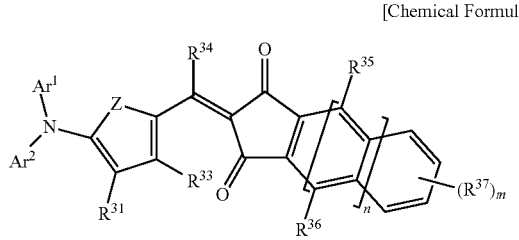

In Chemical Formula 3,

Z is one of S, Se, Te, S(=O), S(=O)$_2$ and SiR$^a$R$^b$ (wherein R$^a$ and R$^b$ is hydrogen or a C1 to C10 alkyl group), Ar$^1$ and Ar$^2$ are one of a substituted or unsubstituted C6 to C30 aryl group and a substituted or unsubstituted C4 to C30 heteroaryl group, R$^{31}$ to R$^{37}$ are independently one of hydrogen, a substituted or unsubstituted C1 to C30 alkyl group, a substituted or unsubstituted C6 to C30 aryl group, a substituted or unsubstituted C4 to C30 heteroaryl group, a halide group, and a cyano group (CN), m is an integer ranging from 0 to 4, and n is 0 or 1.

Ar$^1$ and Ar$^2$ may be a substituted or unsubstituted C6 to C20 aryl group.

At least one of Ar1 and Ar2 may be a naphthyl group or an anthracenyl group.

The compound represented by Chemical Formula 2 may be a compound represented by one of Chemical Formulae 2a to 2e, but is not limited thereto.

[Chemical Formula 2a]

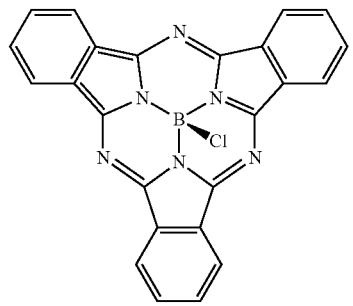

[Chemical Formula 2b]

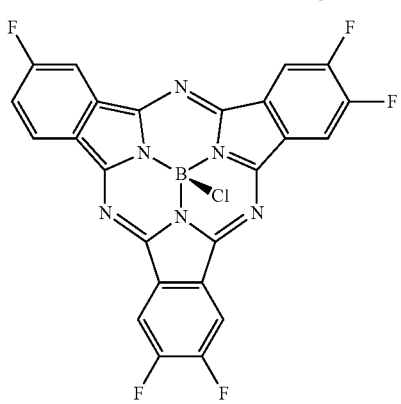

[Chemical Formula 2c]

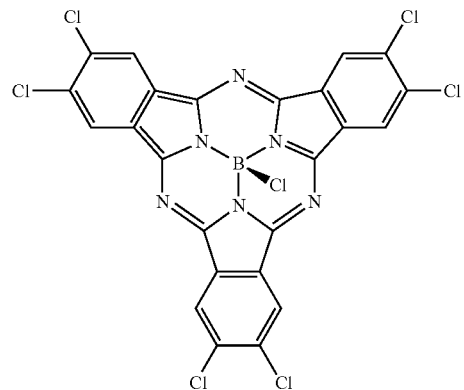

[Chemical Formula 2d]

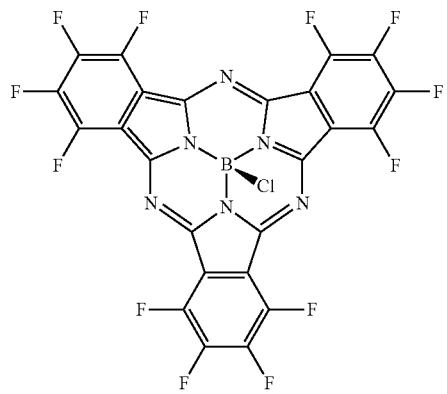

[Chemical Formula 2e]

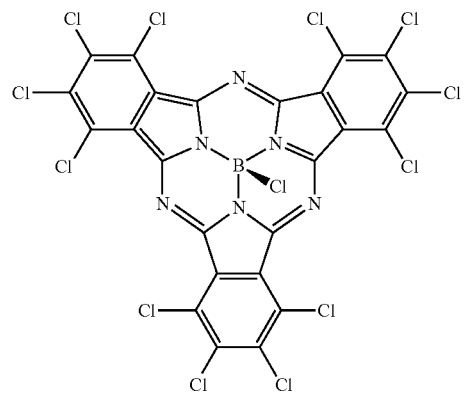

The active layer 30 may improve absorption selectivity for green light by combining an n-type semiconductor compound that does not absorb light in a visible ray region and particularly, that has significantly low absorption or almost no absorption in a blue wavelength region (greater than or equal to about 400 nm to less than about 500 nm) and a p-type semiconductor compound having a maximum absorption wavelength in a green wavelength region and particularly, in a wavelength region of about 500 nm to about 600 nm.

The active layer 30 may exhibit a light absorption curve having a relatively small full width at half maximum (FWHM) of about 50 nm to about 200 nm, about 50 nm to about 150 nm, or about 50 nm to about 120 nm. Herein, the FWHM is a width of a wavelength corresponding to half of a maximum absorption point. As used herein, when specific definition is not otherwise provided, it may be defined by absorbance measured by UV-Vis spectroscopy. Within the FWHM range, selectivity for a green wavelength region may be increased.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the n-type semiconductor compound and the p-type semiconductor compound in a thickness ratio of about 1:100 to about 100:1. The n-type semiconductor compound and the p-type semiconductor compound may be included in a thickness ratio ranging from about 1:50 to about 50:1 within the range, specifically, about 1:10 to about 10:1, and more specifically, about 1:about 1. When the n-type and p-type semiconductor compounds have a composition ratio within the above ranges, an exciton may be effectively produced and a pn junction may be effectively formed.

The p-type layer may include the p-type semiconductor compound, and the n-type layer may include the n-type semiconductor compound.

The active layer 30 may have a thickness of about 1 nm to about 500 nm, and specifically, about 5 nm to about 300 nm. Within the thickness range, the active layer may effectively absorb light, effectively separate holes from electrons, and deliver them, thereby effectively improving photoelectric conversion efficiency.

In the organic photoelectric device 100, when light enters from the first electrode 10 and/or the second electrode 20, and when the active layer 30 absorbs light having a desired, or alternatively predetermined wavelength region, excitons may be produced from the inside. The excitons are separated into holes and electrons in the active layer 30, the separated holes are transported to an anode that is one of the first electrode 10 and second electrode 20 and the separated electrons are transported to the cathode that is the other one of the first electrode 10 and the second electrode 20 so as to flow a current in the organic photoelectric device. The active layer 30 may be configured to selectively absorb light in a green wavelength region.

In general, since a reverse voltage is externally applied to at most sense charges produced by radiating light, counter charges may be injected from an electrode to an active layer due to the externally applied voltage. These counter charges are measured as a dark current, which may increase noises.

The organic photoelectric device 100 includes the active layer 30 including the first and second compounds, and thus may be efficiently blocked from charges flowing in from the outside, as well as have a high photoelectric efficiency. Accordingly, the organic photoelectric device 100 may not only deteriorate photoelectric conversion characteristics, but dark current may also be decreased.

Hereinafter, an organic photoelectric device according to another example embodiment is described referring to FIG. 2.

Figure 2:
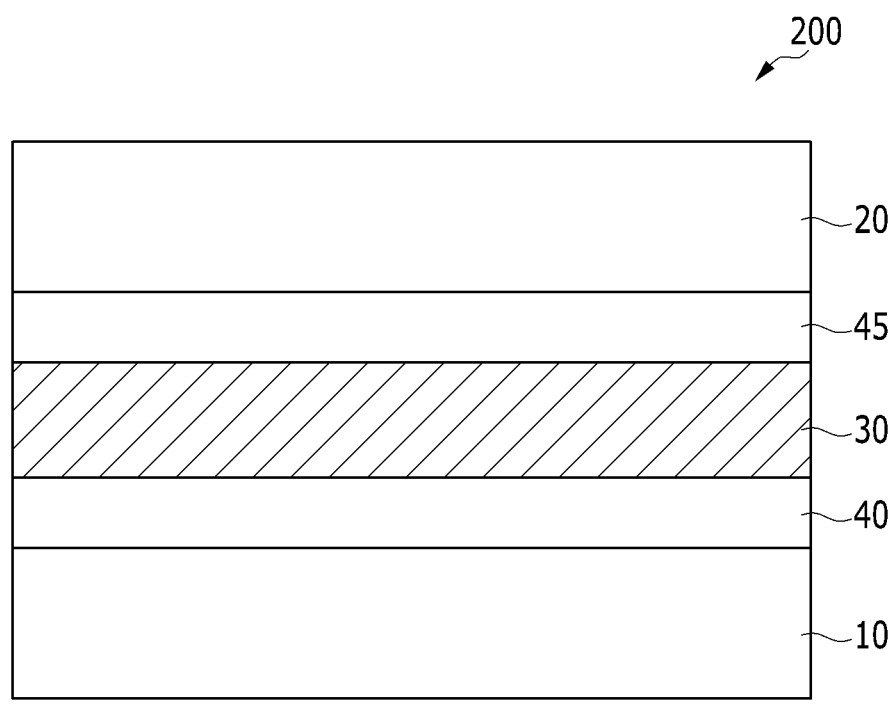
FIG. 2 is a cross-sectional view illustrating an organic photoelectric device according to another example embodiment.

FIG. 2 is a cross-sectional view showing an organic photoelectric device according to another example embodiment.

Referring to FIG. 2, an organic photoelectric device 200 according to the example embodiment includes a first electrode 10 and a second electrode 20 facing each other, and an active layer 30 between the first electrode 10 and the second electrode 20, similarly to the above example embodiment.

However, the organic photoelectric device 200 according to the example embodiment further includes charge auxiliary layers 40 and 45 between the first electrode 10 and the active layer 30, and between the second electrode 20 and the active layer 30, respectively, unlike the above example embodiment. The charge auxiliary layers 40 and 45 may be configured to facilitate the transfer of holes and electrons separated from the active layer 30, so as to increase efficiency.

In general, examples of the charge auxiliary layer may be a hole injection layer (HIL) configured to facilitate hole injection, a hole transport layer (HTL) configured to facilitate hole transport, an electron blocking layer (EBL) reducing or preventing electron transport, an electron injection layer (EIL) configured to facilitate electron injection, an electron transport layer (ETL) configured to facilitate electron transport, and a hole blocking layer (HBL) reducing or preventing hole transport.

However, the organic photoelectric device 200 according to an example embodiment includes the n-type and p-type semiconductor compounds, and thus may block charges flowing in from the outside and does not necessitate a separate hole blocking layer (HBL). Accordingly, generation of a dark current as well as a decrease of photoelectric efficiency caused by formation of multi-layered interfaces may be reduced or prevented.

For example, the charge auxiliary layers 40 and 45 may be at least one of a hole injection layer (HIL) configured to facilitate hole injection, a hole transport layer (HTL) configured to facilitate hole transport, an electron injection layer (EIL) configured to facilitate electron injection, and an electron transport layer (ETL) configured to facilitate electron transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one of, for example, poly(3,4-ethylenedioxythiophene):poly(styrene sulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, Alq3, Gaq3, Inq3, Znq2, Zn(BTZ)2, BeBq2, and a combination thereof, but is not limited thereto.

Either one of the charge auxiliary layers 40 and 45 may be omitted.

In the organic photoelectric device 200, a hole blocking layer may not be between the first electrode 10 and the active layer 30, or between the second electrode 20 and the active layer 30.

The organic photoelectric devices 100 and 200 may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an image sensor is described.

Figure 3:
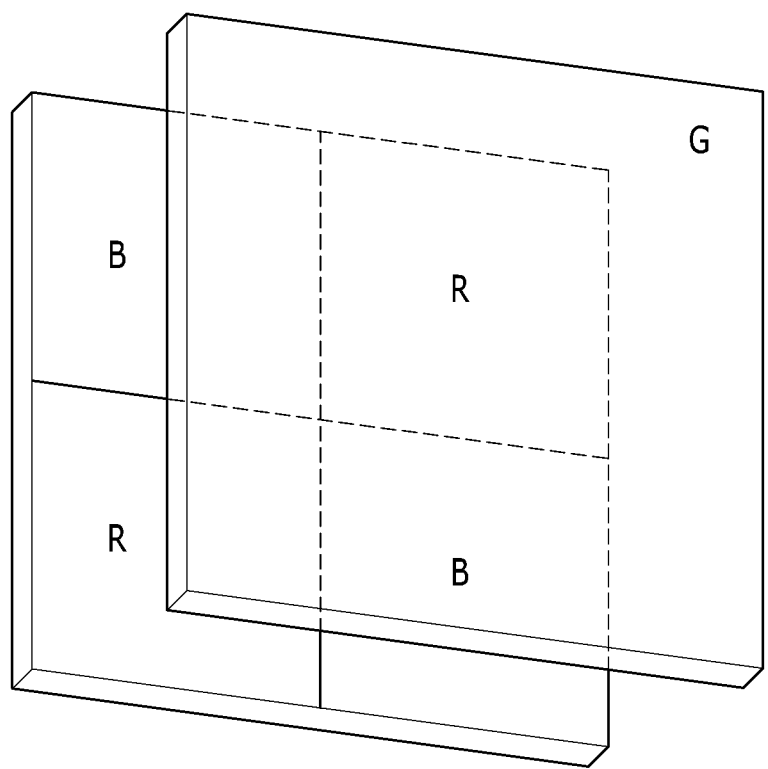
FIG. 3 is a schematic top plan view illustrating an image sensor according to an example embodiment.
Figure 4:
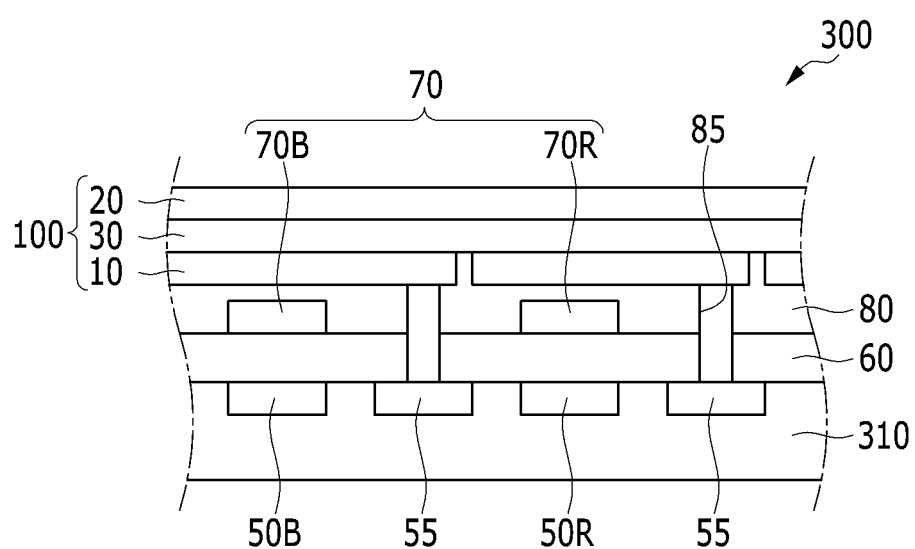
FIG. 4 is a cross-sectional view illustrating the image sensor of FIG. 3.

FIG. 3 is a schematic top plan view showing an image sensor according to an example embodiment, and FIG. 4 is a cross-sectional view of the image sensor of FIG. 3.

Referring to FIGS. 3 and 4, an image sensor 300 according to an example embodiment includes a semiconductor substrate 310 integrated with a first photo-sensing device 50B configured to sense light in a blue wavelength region and a second photo-sensing device 50R configured to sense light in a red wavelength region, a transmission transistor (not shown), and a charge storage 55, a lower insulation layer 60, a color filter layer 70, an upper insulation layer 80, and the organic photoelectric device 100.

The semiconductor substrate 310 may be a silicon substrate, and is integrated with the photo-sensing devices 50B and 50R, the transmission transistor (not shown), and the charge storage 55. The photo-sensing devices 50B and 50R may be photodiodes.

The photo-sensing devices 50B and 50R, the transmission transistor, and/or the charge storage 55 may be integrated in each pixel, and as shown in the drawing, the photo-sensing devices 50B and 50R may be included in a blue pixel and a red pixel and the charge storage 55 may be included in a green pixel.

The photo-sensing devices 50B and 50R may be configured to sense light, the information sensed by the photo-sensing devices may be transferred by the transmission transistor, the charge storage 55 is electrically connected with the organic photoelectric device 100, and the information of the charge storage 55 may be transferred by the transmission transistor.

A metal wire (not shown) and a pad (not shown) may be formed on the semiconductor substrate 310. In order to decrease signal delay, the metal wire and pad may be made of or include a metal having low resistivity, for example, aluminum (Al), copper (Cu), silver (Ag), and alloys thereof, but are not limited thereto. Further, the metal wire and pad are not limited to the structure, and the metal wire and pad may be positioned under the photo-sensing devices 50B and 50R.

The lower insulation layer 60 is formed on the metal wire and the pad. The lower insulation layer 60 may be made of or include an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

The color filter layer 70 is formed on the lower insulation layer 60.

For example, the color filter layer 70 may be positioned between the semiconductor substrate 310 and the organic photoelectric device 100, and may include a first color filter 71 that is positioned corresponding to the first photo-sensing device 50B and configured to selectively transmit light in a blue wavelength region, and a second color filter 72 that is positioned corresponding to the second photo-sensing device 50R and is configured to selectively transmit light in a red wavelength region. For example, the first color filter 71 may be a blue filter and the second color filter 72 may be a red filter.

The color filter layer 70 may be positioned on the organic photoelectric device 100, unlike FIG. 4. In this case, the color filter layer 70 may include a first color filter corresponding to the first photo-sensing device and configured to selectively transmit light in blue and green regions, and a second color filter corresponding to the second photo-sensing device and configured to selectively transmit light in red and green regions. For example, the first color filter may be or include a cyan filter, and the second color filter may be or include a yellow filter.

The upper insulation layer 80 is formed on the color filter layer 70. The upper insulation layer 80 reduces or substantially eliminates a step caused by the color filter layer 70, and smoothens the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 may include the n-type semiconductor compound being transparent in a visible ray region and represented by Chemical Formula 1, and the p-type semiconductor compound having a maximum absorption wavelength in a wavelength region of about 500 nm to about 600 nm of a visible ray region, as described above.

The active layer 30 may be configured to selectively absorb light in a green wavelength region and may replace a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

According to an example embodiment, a hole blocking layer may not be between the first electrode 10 and the active layer 30, or between the second electrode 20 and the active layer 30, and thereby a size of an image sensor may be decreased and a down-sized image sensor may be realized.

Referring to FIG. 4, an image sensor 300 includes a first photo-sensing device 50B configured to sense light in a blue wavelength region and a second photo-sensing device 50R configured to sense light in a red wavelength region, wherein the first photo-sensing device 50B and the second photo-sensing device 50R may be spaced apart from each other in a horizontal direction at substantially equivalent depths from the surface of the semiconductor substrate 310.

Figure 5:
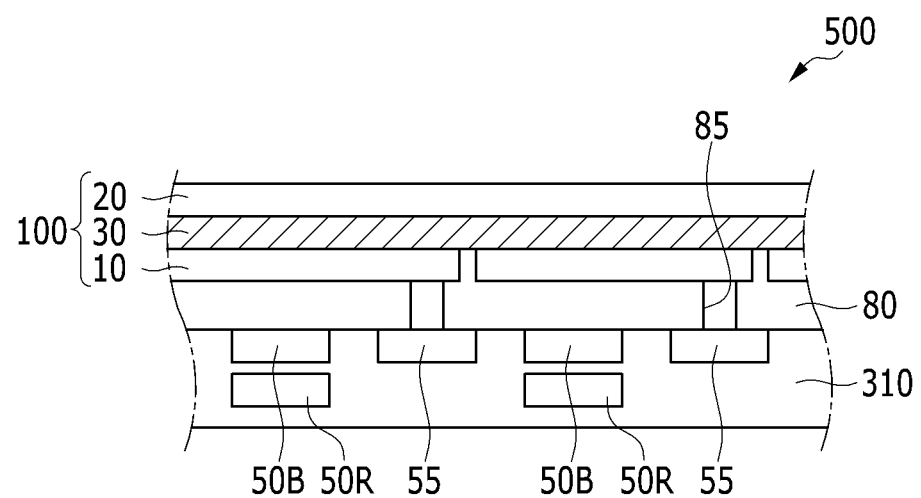
FIG. 5 is another cross-sectional view illustrating the image sensor of FIG. 3.

Referring to FIG. 5, an image sensor 400 includes a first photo-sensing device 50B and a second photo-sensing device 50R positioned at different depths from the surface of the semiconductor substrate 310. That is, the second photo-sensing device 50R that is configured to sense light in a long wavelength region may be positioned more deeply from the surface of the semiconductor substrate 310 than the first photo-sensing device 50B that is configured to sense light in a shorter wavelength region. The first photo-sensing device 50B and the second photo-sensing device 50R may be configured to selectively absorb light in each wavelength region depending on a stack depth. Accordingly, unlike the example embodiment, the color filter layer 70 may be omitted.

Referring to FIGS. 4 and 5, the first photo-sensing device 50B that is configured to sense light in a blue wavelength region and the second photo-sensing device 50R that is configured to sense light in a red wavelength region are integrated in the semiconductor substrate 310, and the organic photoelectric device 100 includes an organic active layer 30 configured to selectively absorb light in a green wavelength region. However, the organic photoelectric device 100 is not limited to the above structure shown in FIG. 2. The following structures may be included in example embodiments: a photo-sensing device configured to sense light in a blue wavelength region and a photo-sensing device configured to sense light in a green wavelength region may be integrated in the semiconductor substrate 310, and the organic photoelectric device 100 includes an organic active layer 30 configured to selectively absorb light in a red wavelength region; or alternatively, a photo-sensing device configured to sense light in a red wavelength region and a photo-sensing device configured to sense light in a green wavelength region may be integrated in the semiconductor substrate 310, and the organic photoelectric device 100 includes an organic active layer 30 configured to selectively absorb light in a blue wavelength region.

Herein, the red wavelength region may have, for example, a maximum absorption wavelength (Amax) that is greater than about 580 nm and less than or equal to about 700 nm, the blue wavelength region may have, for example, a maximum absorption wavelength (Amax) that is greater than or equal to about 400 nm and less than about 500 nm, and the green wavelength region may have, for example, a maximum absorption wavelength (Amax) that is about 500 nm to about 580 nm.

In FIGS. 4 and 5, the image sensors 300 and 400 include the organic photoelectric device 100, but the image sensors 300 and 400 may alternatively include the organic photoelectric device 200 instead.

Figure 6:
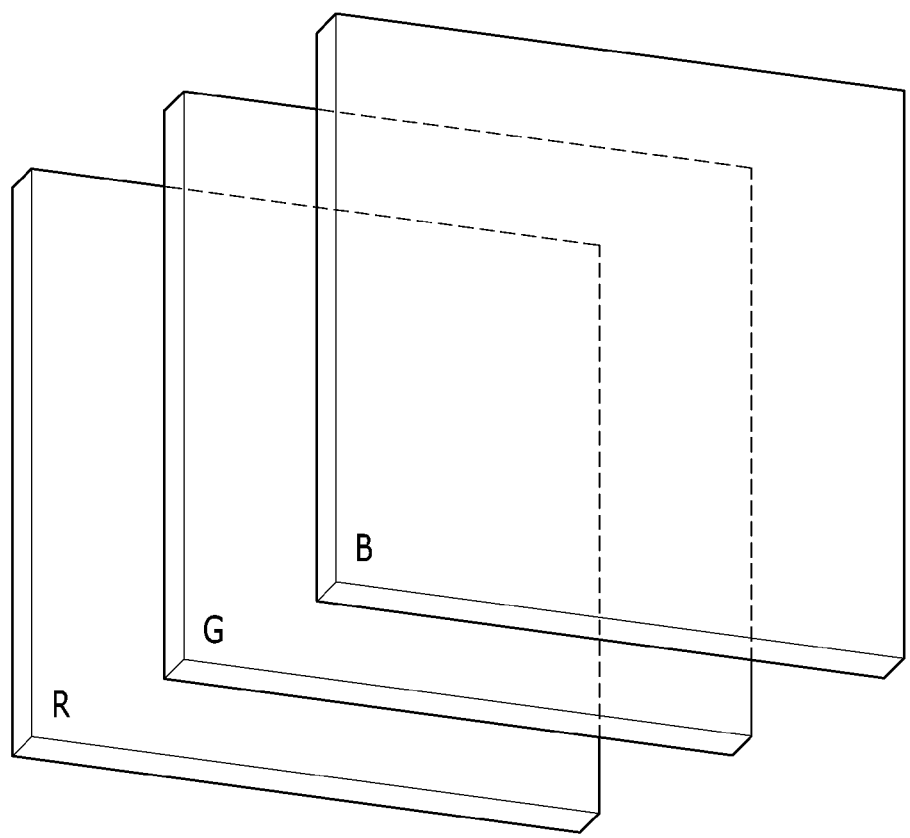
FIG. 6 is a schematic top plan view illustrating an image sensor according to another example embodiment.

FIG. 6 is a schematic top plan view showing an image sensor according to another example embodiment.

The image sensor according to the example embodiment includes a green photoelectronic device configured to selectively absorb light in a green wavelength region, a blue photoelectronic device configured to selectively absorb light in a blue wavelength region, and a red photoelectronic device configured to selectively absorb light in a red wavelength region, the green photoelectronic device, the blue photoelectronic device and the red photoelectronic device being stacked.

In FIG. 6, the red photoelectronic device, the green photoelectronic device, and the blue photoelectronic device are sequentially stacked, but the stack order may be changed without limitation.

The green photoelectronic device may be one of the above organic photoelectronic devices 100 and 200, the blue photoelectronic device may include electrodes facing each other and an active layer interposed therebetween and including an organic material configured to selectively absorb light in a blue wavelength region, and the red photoelectronic device may include electrodes facing each other and an active layer interposed therebetween and including an organic material configured to selectively absorb light in a red wavelength region.

As described above, the organic photoelectronic device configured to selectively absorb light in a red wavelength region, the organic photoelectronic device configured to selectively absorb light in a green wavelength region, and the organic photoelectronic device configured to selectively absorb light in a blue wavelength region are stacked on each other, and thereby a size of an image sensor may be decreased and a down-sized image sensor may be realized.

Hereinafter, the example embodiments are illustrated in more detail with reference to examples. However, these embodiments are examples and the example embodiments are not limited thereto.

Synthesis Example 1: Synthesis of n-Type Semiconductor Compound

One equivalent of pyromellitic dianhydride and 2.5 equivalent of aniline are dissolved in DMF, and the solution is heated and stirred at 150° C. for 2 hours. Then, a precipitate produced therein is filtered, obtaining an n-type semiconductor compound represented by Chemical Formula 1a-1 (yield: 78%).

$^1$H NMR (300 MHz, DMSO-d6) 8.42 (s, 2H), 7.58-7.43 (m, 10H)

[Chemical Formula 1a-1]

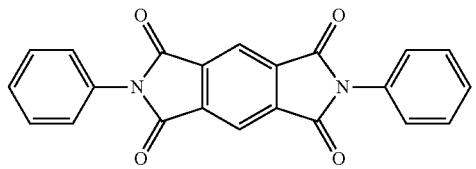

Synthesis Example 2: Synthesis of n-Type Semiconductor Compound

An n-type semiconductor compound represented by Chemical Formula 1a-2 is obtained according to the same method as Synthesis Example 1 except for using 2-aminopyridine instead of aniline (yield: 38%).

[Chemical Formula 1a-2]

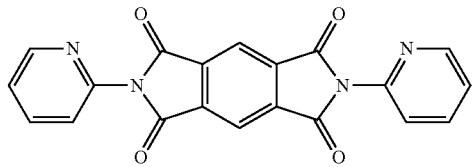

$^1$H NMR (300 MHz, DMSO-d6) 8.70 (d, 2H), 8.64 (s, 2H), 8.11 (t, 2H), 7.62-7.57 (m, 4H)

Synthesis Example 3: Synthesis of n-Type Semiconductor Compound

An n-type semiconductor compound represented by Chemical Formula 1a-3 is obtained according to the same method as Synthesis Example 1 except for using 3-aminopyridine instead of aniline (yield: 71%).

[Chemical Formula 1a-3]

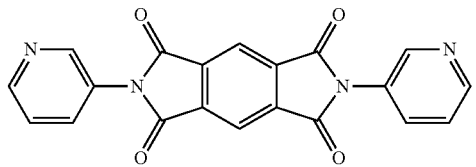

$^1$H NMR (300 MHz, DMSO-d6) 8.80 (s, 2H), 8.70 (d, 2H), 8.48 (s, 2H), 7.95 (d, 2H), 7.66 (t, 2H)

Synthesis Example 4: Synthesis of n-Type Semiconductor Compound

An n-type semiconductor compound represented by Chemical Formula 1a-4 is obtained according to the same method as Synthesis Example 1 except for using 4-aminopyridine instead of aniline (yield: 41%).

[Chemical Formula 1a-4]

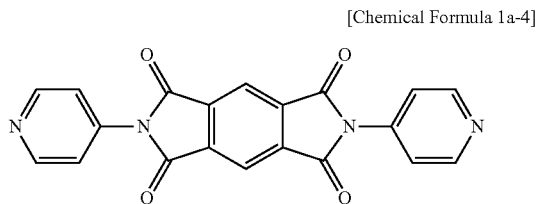 [SMILES: O=c1c2cc3c(=O)n(-c4ccncc4)c(=O)c3cc2c(=O)n1-c1ccncc1]

¹H NMR (300 MHz, DMSO-d6) 8.80 (d, 4H), 8.48 (s, 2H), 7.64 (d, 4H)

Synthesis Example 5: Synthesis of n-Type Semiconductor Compound

An n-type semiconductor compound represented by Chemical Formula 1a-5 is obtained according to the same method as Synthesis Example 1 except for using 3,3',4,4'-biphenyltetracarboxylic dianhydride instead of pyromellitic dianhydride (yield: 75%).

[Chemical Formula 1d-1]

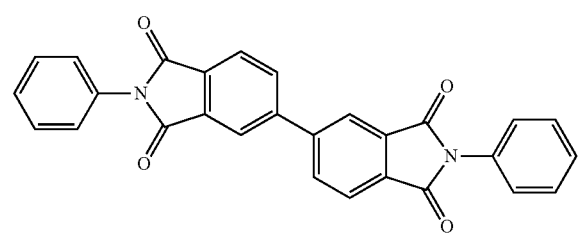

¹H NMR (300 MHz, DMSO-d6) 8.50 (s, 2H), 8.44 (d, 2H), 8.15 (d, 2H), 7.60-7.50 (m, 6H), 7.40 (d, 2H)

Synthesis Example 6: Synthesis of n-Type Semiconductor Compound

An n-type semiconductor compound represented by Chemical Formula 1d-2 is obtained according to the same method as Synthesis Example 1 except for using 3,3',4,4'-biphenyltetracarboxylic anhydride instead of pyromellitic dianhydride and 2-aminopyridine instead of aniline (yield: 76%).

[Chemical Formula 1d-2]

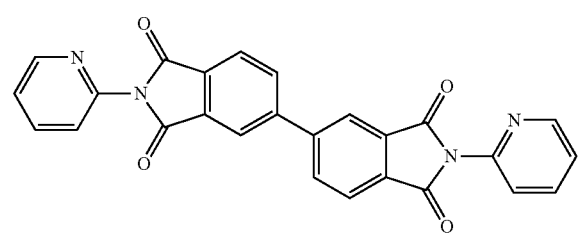

¹H NMR (300 MHz, DMSO-d6) 8.67 (d, 2H), 8.50 (s, 2H), 8.44 (d, 2H), 8.14 (s, 2H), 8.08 (t, 2H), 7.60 (d, 2H), 7.56 (t, 2H)

Synthesis Example 7: Synthesis of n-Type Semiconductor Compound

An n-type semiconductor compound represented by Chemical Formula 1d-3 is obtained according to the same method as Synthesis Example 1 except for using 3,3',4,4'-biphenyl tetracarboxylic anhydride instead of pyromellitic dianhydride and 3-aminopyridine instead of aniline (yield: 79%).

[Chemical Formula 1d-3]

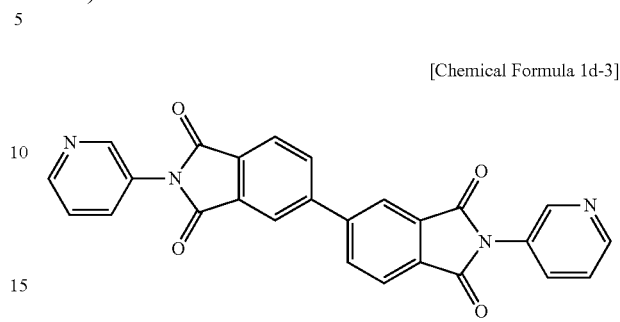

¹H NMR (300 MHz, DMSO-d6) 8.73 (s, 2H), 8.66 (d, 2H), 8.50 (s, 2H), 8.44 (d, 2H), 8.15 (d, 2H), 7.97 (d, 2H), 7.63 (t, 2H)

Synthesis Example 8: Synthesis of n-Type Semiconductor Compound

An n-type semiconductor compound represented by Chemical Formula 1d-4 is obtained according to the same method as Synthesis Example 1 except for using 3,3',4,4'-biphenyl tetracarboxylic anhydride instead of pyromellitic dianhydride and 4-aminopyridine instead of aniline (yield: 79%).

[Chemical Formula 1d-4]

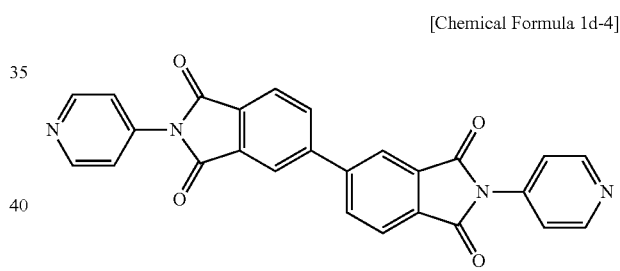

¹H NMR (300 MHz, DMSO-d6) 8.76 (d, 4H), 8.52 (s, 2H), 8.44 (d, 2H), 8.15 (d, 2H), 7.62 (d, 4H)

Synthesis Example 9: Synthesis of n-Type Semiconductor Compound

An n-type semiconductor compound represented by Chemical Formula 1e-1 is obtained according to the same method as Synthesis Example 1 except for using 1,4,5,8-naphthalene tetracarboxylic dianhydride instead of pyromellitic dianhydride (yield: 70%).

[Chemical Formula 1e-1]

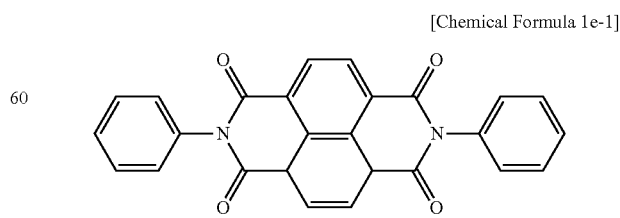

¹H NMR (300 MHz, DMSO-d6) 8.72 (d, 4H), 7.59-7.45 (m, 10H)

Synthesis Example 10: Synthesis of n-Type Semiconductor Compound

An n-type semiconductor compound represented by Chemical Formula 1e-2 is obtained according to the same method as Synthesis Example 1 except for using 3,3',4,4'-biphenyl tetracarboxylic anhydride instead of pyromellitic dianhydride and 2-aminopyridine instead of aniline (yield: 35%).

[Chemical Formula 1e-2]

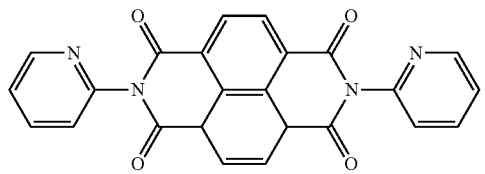

$^1$H NMR (300 MHz, DMSO-d6) 8.71 (d, 4H), 8.47 (s, 2H), 8.22-8.10 (m, 4H), 7.40 (t, 2H)

Synthesis Example 11: Synthesis of n-Type Semiconductor Compound

An n-type semiconductor compound represented by Chemical Formula 1e-3 is obtained according to the same method as Synthesis Example 1 except for using 3,3',4,4'-biphenyltetracarboxylic anhydride instead of pyromellitic dianhydride and 3-aminopyridine instead of aniline (yield: 22%).

[Chemical Formula 1e-3]

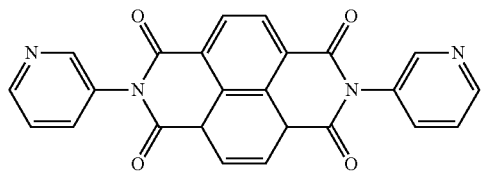

$^1$H NMR (300 MHz, DMSO-d6) 8.73 (d, 4H), 8.12 (d, 2H), 7.76 (t, 2H), 7.51 (d, 2H), 7.31 (t, 2H)

Synthesis Example 12: Synthesis of n-Type Semiconductor Compound

An n-type semiconductor compound represented by Chemical Formula 1e-4 is obtained according to the same method as Synthesis Example 1 except for using 3,3',4,4'-biphenyltetracarboxylic anhydride instead of pyromellitic dianhydride and 4-aminopyridine instead of aniline (yield: 97%).

[Chemical Formula 1e-4]

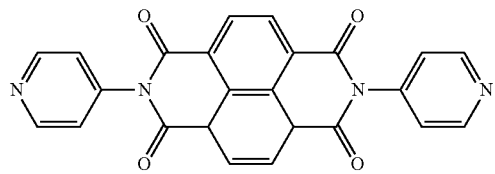

$^1$H NMR (300 MHz, DMSO-d6) 8.81 (d, 4H), 8.72 (d, 4H), 7.70 (d, 4H)

Light Absorption Characteristics

Light absorption characteristics of the compounds according to Synthesis Examples 1 to 12 depending on a wavelength are evaluated. The light absorption characteristics are evaluated in a thin film state. The light absorption characteristics are evaluated by thermally evaporating each compound according to Synthesis Examples 1 to 12 at a rate of 0.5-1.0 Å/s under high vacuum (<10$^{-7}$ Torr) to form 70 nm-thick thin films, and radiating a ultraviolet (UV)-visible ray (UV-Vis) to the thin films by using Cary 5000 UV spectroscopy (Varian Medical System).

TABLE 1

| Compound | Relative absorption ratio in 400-500 nm (%)* | HOMO (eV) | LUMO** (eV) |
|---|---|---|---|
| Synthesis Example 1 | 62 | 6.64 | 3.00 |
| Synthesis Example 2 | 60 | 7.01 | 3.43 |
| Synthesis Example 3 | 53 | 6.96 | 3.43 |
| Synthesis Example 4 | 55 | 7.18 | 3.71 |
| Synthesis Example 5 | 40 | 6.46 | 3.11 |
| Synthesis Example 6 | 38 | 6.77 | 3.35 |
| Synthesis Example 7 | 28 | 6.64 | 3.29 |
| Synthesis Example 8 | 30 | 7.02 | 3.65 |
| Synthesis Example 9 | 52 | 6.95 | 4.17 |
| Synthesis Example 10 | 49 | 6.94 | 4.08 |
| Synthesis Example 11 | 40 | 7.08 | 4.20 |
| Synthesis Example 12 | 42 | 7.16 | 4.37 |
| C60 | 100 | 6.29 | 4.22 |

*Relative absorption rate when C60 has an absorption rate of 100%

**LUMO is Lowest Unoccupied Molecular Orbital

Referring to Table 1, the compounds according to Synthesis Examples 1 to 12 in a thin film state exhibit a very low absorption rate in a wavelength region ranging from about 400 nm to about 500 nm compared with C60. In addition, the compounds according to Synthesis Examples 1 to 12 have a HOMO level in a range of 6.64 eV to 7.18 eV and may be blocking a hole.

Manufacture of Organic Photoelectric Device

Example 1

An about 100 nm-thick anode is formed by sputtering ITO on a glass substrate, and a 5 nm-thick charge auxiliary layer is formed thereon by laminating molybdenum oxide (MoOx, 0<x≤3) and an aluminum thin film. Subsequently, an 80 nm-thick active layer is formed by co-depositing the compound according to Synthesis Example 1 as an n-type semiconductor compound and a compound represented by Chemical Formula 4a (2-((5-(naphthalen-1-yl(phenyl)amino)selenophen-2-yl)methylene)-1H-indene-1,3(2H)-dione) as a p-type semiconductor compound) in a thickness ratio of 1:1 on the molybdenum oxide:aluminum thin film. Subsequently, an 80 nm-thick cathode is formed by sputtering ITO on the active layer, manufacturing an organic photoelectric device.

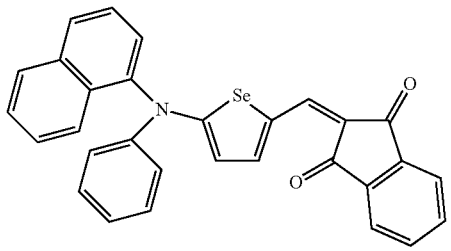

[Chemical Formula 4a]

Examples 2 to 12

Each organic photoelectric device is manufactured according to the same method as Example 1 except for respectively using the n-type semiconductor compounds according to Synthesis Examples 2 to 12 instead of the n-type semiconductor compound according to Synthesis Example 1.

Comparative Example 1

An organic photoelectric device is manufactured according to the same method as Example 1 except for using C60 instead of the n-type semiconductor compound according to Synthesis Example 1.

External Quantum Efficiency

External quantum efficiency (EQE) of each organic photoelectric device according to Examples 1 to 12 and Comparative Example 1 depending on a wavelength is evaluated.

The external quantum efficiency is measured by using an incident Photon to Charge Carrier Efficiency (IPCE) measurement system (McScience Inc., Korean). First of all, the equipment is calibrated by using a Si photodiode (Hamamatsu Photonics K.K. Japan) and mounted on each organic photoelectric device according to Examples 1 to 12 and Comparative Example 1, and its external quantum efficiency is measured at a wavelength ranging from about 350 nm to about 750 nm.

TABLE 2

| Example No. | $\lambda_{max}$ (nm) | $\dfrac{EQE@450\ nm}{EQE@\lambda max} \times 100\,(\%)$ |
| --- | --- | --- |
| Example 1 | 550 | 23 |
| Example 2 | 550 | 21 |
| Example 3 | 550 | 18 |
| Example 4 | 550 | 18 |
| Example 5 | 535 | 17 |
| Example 6 | 535 | 15 |
| Example 7 | 535 | 12 |
| Example 8 | 535 | 13 |
| Example 9 | 540 | 20 |
| Example 10 | 540 | 19 |
| Example 11 | 540 | 17 |
| Example 12 | 540 | 19 |
| Comparative Example 1 | 530 | 35 |

Referring to Table 2, the organic photoelectric devices according to Examples 1 to 12 exhibit a maximum absorption wavelength in a green light region and considerably decreased efficiency in a blue wavelength region of about 450 nm compared with the organic photoelectric device according to Comparative Example 1. The reason for the decreased efficiency is that the compounds according to Synthesis Examples 1 to 12 exhibit an absorption rate in a blue wavelength region of about 450 nm.

While this disclosure has been described in connection with what is presently considered to be example embodiments, it is to be understood that the invention is not limited to the example embodiments, but, on the contrary, is intended to cover various modifications and equivalent arrangements included within the spirit and scope of the appended claims.

What is claimed is:

1. An organic photoelectric device comprising:
   a first electrode and a second electrode facing each other, and
   an active layer between the first electrode and the second electrode,
   wherein the active layer includes,
   an n-type semiconductor compound that is transparent in a visible ray region and represented by Chemical Formula 1, the n-type semiconductor compound being configured to not substantially absorb visible light in a wavelength region that is greater than or equal to about 400 nm and less than or equal to about 700 nm, and
   a p-type semiconductor compound represented by Chemical Formula 3, wherein the p-type semiconductor compound has a maximum absorption wavelength in a wavelength region of about 500 nm to about 600 nm of a visible ray region:

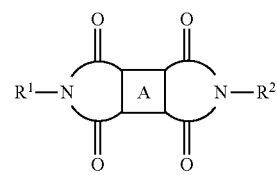

[Chemical Formula 1]

wherein, in Chemical Formula 1,
A is one of a substituted or unsubstituted C6 to C30 aromatic ring group, a substituted or unsubstituted C4 to C30 alicyclic group, a substituted or unsubstituted C3 to C30 hetero aromatic ring group, a substituted or unsubstituted C4 to C30 heteroalicyclic group, and a combination thereof, and
$R^1$ and $R^2$ are independently one of a substituted or unsubstituted C6 to C30 aryl group, a substituted or unsubstituted C3 to C30 heteroaryl group, and a combination thereof;

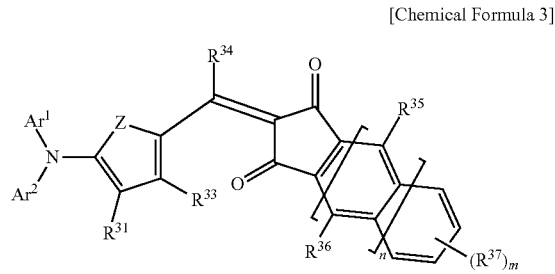

[Chemical Formula 3]

wherein in Chemical Formula 3,
Z is one of S, Se, Te, S(=O), S(=O)$_2$, and SiR$^a$R$^b$ (wherein R$^a$ and R$^b$ is hydrogen or a C1 to C10 alkyl group), Ar¹ and Ar² are one of a substituted or unsubstituted C6 to C30 aryl group and a substituted or unsubstituted C4 to C30 heteroaryl group, R³¹ to R³⁷ are independently one of hydrogen, a substituted or unsubstituted C1 to C30 alkyl group, a substituted or unsubstituted C6 to C30 aryl group, a substituted or unsubstituted C4 to C30 heteroaryl group, a halide group, and a cyano group (CN), m is an integer ranging from 0 to 4, and n is 0 or 1.

2. The organic photoelectric device of claim 1, wherein the n-type semiconductor compound has an energy bandgap that is greater than or equal to about 2.8 eV.

3. The organic photoelectric device of claim 1, wherein the n-type semiconductor compound has a HOMO level that is greater than about 6.0 eV.

4. The organic photoelectric device of claim 1, wherein a difference between a HOMO level of the n-type semiconductor compound and a work function of the second electrode is greater than or equal to about 1.5 eV.

5. The organic photoelectric device of claim 1, wherein the n-type semiconductor compound is represented by one of Chemical Formulae 1a to 1e:

[Chemical Formula 1a]
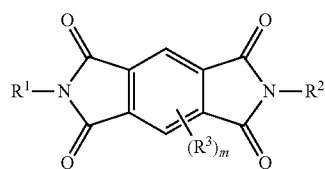

[Chemical Formula 1b]
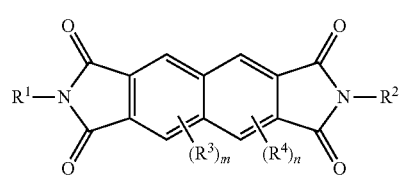

[Chemical Formula 1c]
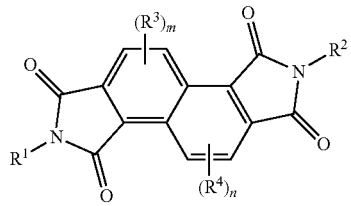

[Chemical Formula 1d]
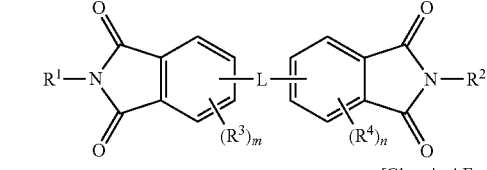

[Chemical Formula 1e]
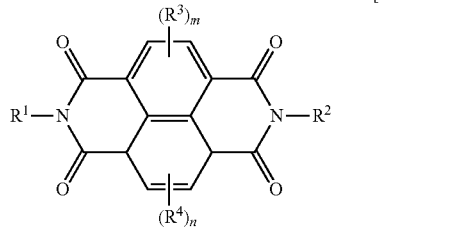

wherein in Chemical Formulae 1a to 1e,

R³ and R⁴ are independently one of a halogen, a C1 to C10 haloalkyl group, a nitro group, a cyano group, a C1 to C10 alkoxy group, and a C1 to C10 alkyl group, L is one of a C1 to C4 alkylene, a fluoro-substituted C1 to C4 alkylene, phenylene, S, S(=O), S(=O)₂, O, and C(=O), and m and n are independently an integer ranging from 0 to 2.

6. The organic photoelectric device of claim 1, wherein the p-type semiconductor compound has an energy bandgap that is greater than or equal to about 2.0 eV and less than or equal to about 2.5 eV.

7. The organic photoelectric device of claim 1, wherein the p-type semiconductor compound has a maximum absorption wavelength (λmax) that is greater than or equal to about 530 nm and less than or equal to about 600 nm.

8. The organic photoelectric device of claim 1, wherein the active layer is configured to selectively absorb light in a green wavelength region.

9. The organic photoelectric device of claim 1, wherein a hole blocking layer is not present between the first electrode and the active layer or between the second electrode and the active layer.

10. An image sensor including the organic photoelectric device of claim 1.

11. The image sensor of claim 10, wherein the image sensor comprises a semiconductor substrate integrated with a first photo-sensing device configured to sense light in a blue wavelength region and a second photo-sensing device configured to sense light in a red wavelength region, and the organic photoelectric device on the semiconductor substrate is configured to absorb light in a green wavelength region.

12. The image sensor of claim 11, wherein the first photo-sensing device and the second photo-sensing device are at a different depth from a surface of the semiconductor substrate.

13. The image sensor of claim 11, wherein the image sensor further comprises a color filter layer on or under the organic photoelectric device.

14. The image sensor of claim 13, wherein the color filter layer is between the semiconductor substrate and the organic photoelectric device and comprises:

a first color filter corresponding to the first photo-sensing device and configured to selectively transmit light in a blue region, and a second color filter corresponding to the second photo-sensing device and configured to selectively transmit light in a red region.

15. The organic photoelectric device of claim 1, wherein the hydrogen of each ring of Chemical Formula A is replaced by a substituent selected from a C1 to C10 linear or branched alkyl group, a halogen, and a cyano group.

16. The organic photoelectric device of claim 1, wherein R¹ and R² are represented by Chemical Formula A:

[Chemical Formula A]

(1)

(2)
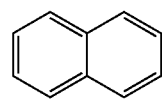

(3)
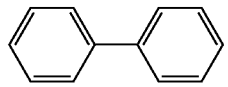

(4) 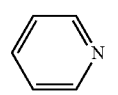
(5) 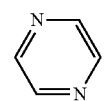
(6) 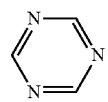
(7) 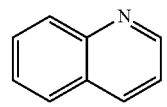
(8) 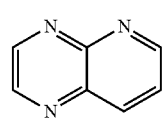
(9) 
(10) 
(11) 
(12) 
wherein, in Chemical Formula A,
$X^a$, $X^b$, $X^c$ and $X^d$ are independently one of O, S, Se, Te, S(=O), S(=O)$_2$, and SiR$^a$R$^b$ (R$^a$ and R$^b$ being hydrogen or a C1 to C10 alkyl group).
* * * * *